(12) United States Patent
Harpster

(10) Patent No.: US 6,242,668 B1
(45) Date of Patent: Jun. 5, 2001

(54) STRAWBERRY ENDO-1,4-β-GLUCANASE GENES AND THEIR USES

(75) Inventor: Mark H. Harpster, Albany, CA (US)

(73) Assignee: DNA Plant Technology Corporation, Oakland, CA (US)

(*) Notice: Subject to any disclaimer, the term of this patent is extended or adjusted under 35 U.S.C. 154(b) by 0 days.

(21) Appl. No.: 09/348,443

(22) Filed: Jul. 7, 1999

Related U.S. Application Data

(60) Provisional application No. 60/095,606, filed on Aug. 6, 1998.

(51) Int. Cl.$^7$ .......................... C12N 15/29; C12N 15/56; C12N 15/82; A01H 1/00; A01H 5/00
(52) U.S. Cl. .......................... 800/290; 435/419; 435/468; 536/23.6; 800/260; 800/286; 800/287; 800/298
(58) Field of Search .......................... 435/69.1, 320.1, 435/410, 419, 468; 536/24.1, 23.6; 800/278, 286, 287, 290, 295, 298, 260

(56) References Cited

U.S. PATENT DOCUMENTS 6,005,092 * 12/1999 Shoseyov et al. .................. 536/23.6

FOREIGN PATENT DOCUMENTS

WO 97/27295 * 7/1997 (WO) ............................. C12N/15/11

OTHER PUBLICATIONS

Cass et al, Mol. Gen. Genet., vol. 223, pp. 76–86, 1990.*

* cited by examiner

*Primary Examiner*—Gary Benzion
*Assistant Examiner*—Ashwin D. Mehta
(74) *Attorney, Agent, or Firm*—Townsend and Townsend and Crew

(57) ABSTRACT

The invention provides nucleic acid molecules and methods useful in controlling cell wall degradation in plants.

22 Claims, No Drawings

STRAWBERRY ENDO-1,4-β-GLUCANASE GENES AND THEIR USES

CROSS REFERENCE TO RELATED APPLICATIONS

This application claims priority to U.S. Ser. No. 60/095,606, filed Aug. 6, 1998, herein incorporated by reference in its entirety.

FEDERALLY SPONSORED RESEARCH OR DEVELOPMENT

Not applicable.

FIELD OF THE INVENTION

The present invention is directed to plant genetic engineering. In particular, it relates to modulation of expression of strawberry genes encoding endo-1,4-β-glucanases.

BACKGROUND OF THE INVENTION

Fruit ripening is a complex developmental program in which senescing tissues undergo programmed changes in firmness, texture, coloration, flavor and susceptibility to microbial infection. Changes in firmness and texture are largely attributed to alterations in the composition and structure of cell wall polysaccharides. As these modifications influence the post-harvest properties (i.e. storage time and expense, handling damage, desirability to the consumer) of important food crops and, consequently, are of great commercial importance, research in recent years has focused on identifying enzyme activities which are rate-limiting in the promotion of fruit deterioration. In the climacteric species, which are characterized by the autocatalytic production of the ripening hormone ethylene and a ripening-related transient burst in $CO_2$ evolution, the antisense suppression of ACC synthase (Oeller et al., *Science* 254:437–439 (1991)) and ACC oxidase (Picton et al., *Plant J* 3:469 (1993)) in tomato has provided fruit in which ripening and softening can be controlled by the application of ethylene. Similar approaches have been taken in efforts to diminish the activities of cell wall-associated hydrolases (Sheehy et al., *Proc Natl Acad Sci USA* 85:8805–8809 (1988); Smith et al., *Nature* 334:724–726 (1988)), which may play a central role in fruit cell wall breakdown during ripening (Brady C J, *Annu Rev Plant Physiol* 38:155–178 (1987)).

In the non-climacteric species such as strawberry (*Fragaria x ananassa*), much less is known about the ripening process. As these plants lack a respiratory climacteric and ethylene appears to play little, if any role, in fruit ripening, there is growing interest in identifying the factor(s) which mediates ripening. Strawberry fruit exhibit low level ethylene production which is rather constant during ripening (Knee et al., *J Exp Bot* 28:377–39 (1977)), and there is no observable stimulation of ripening upon applying exogenous ethylene (Iwata et al., *J Jap Soc Hort Sci* 38:64–72 (1969)). Although there is no evidence for a ripening-related role for ethylene, strawberry fruit ripening has been shown to be negatively regulated by auxins which originate in the receptacle-born achenes (Given et al., *Planta* 174:402–406 (1988b); Manning K *Planta* 194:62–68 (1994)). As auxin levels decline, fruit exhibit a characteristic ripening profile, one of the major hallmarks of which is rapid deterioration once fruit achieve the red ripe stage. In general, strawberry fruit ripening is typified by the induction of enzyme markers for anthocyanin pigment biosynthesis (e.g. phenylalanine ammonia lyase), a concomitant decrease in chlorophyll and increase in anthocyanin pigments, and a progressive decrease in tissue firmness (Woodward JR *J Sci Food Agric* 23:465–473 (1972); Given et al., *J Plant Physiol* 133:25–30 (1988a)).

Efforts to reveal the molecular basis of changes in firmness, which is a major contributing factor to fruit quality, have focused on cell wall-associated enzymes which are believed to mediate and/or contribute to cell wall breakdown. The most studied of these activities, endopolygalacturonase, is absent, or below the limit of detection, in ripening strawberry fruit (Neal G E *J Sci Food Agri* 16:604–608 (1965); Barnes et al. *J Food Sci* 41:1392–1395 (1976); Huber Dj *J Food Sci* 49:1310–1315 (1984)). Although strawberry fruit is a rich source of pectin, this observation is consistent with cell wall studies which have shown that total extractable polyuronides remain constant as a proportion of cell wall material during ripening and do not show detectable depolymerization (Huber Dj *J Food Sci* 49:1310–1315 (1984)). In contrast to these findings, however, the hemicellulosic fraction of cell walls prepared from ripening fruit demonstrates a progressive shift from high molecular weight to low molecular weight polymers (Huber Dj *J Food Sci* 49:1310–1315 (1984)). While there is no discernible change in the neutral sugar composition of hemicelluloses isolated from stages ranging from small green to red ripe, the average net molecular weight change is quite dramatic; suggestive of an active, developmentally regulated endohydrolyase. Interestingly, this observed hemicellulose depolymerization correlates well with a soluble CMCase activity measured in extracts prepared from ripening strawberry fruit (Barnes et al. *J Food Sci* 41:1392–1395 (1976)). In ripening avocado (HatCel11d and Nevins, 1986) and pepper (Harpster et al., *Plant Mol Biol* 33:47–59 (1997)) fruit, CMCase activity is attributed to an endo-1,4-β-glucanase (EGase; EC 3.2.1.4).

Although largely correlative, there is considerable evidence for the importance of EGases in a wide variety of physiological processes involving changes in cell wall architecture which range from cell wall expansion to disassembly (see review by Brummell et al., 1994). In abscission zone formation, for instance, the infusion of antiserum raised against an abscission zone-related EGase into explants which had been induced to abscise by ethylene was observed to inhibit cell separation (Sexton et al., *Nature* 283:8743–8744 (1980)). Furthermore, the induction of EGase gene expression in fruit of tomato (Lashbrook et al., *Plant Cell* 6:1485–1493 (1994)), avocado (Christoffersen et al. *Plant Mol Biol* 3:385–391 (1984)) and pepper (Ferrarese et al., *Plant Mol Biol* 29:735–747 (1995); Harpster et al., *Plant Mol Biol* 33:47–59 (1997)) correlates well with the onset and development of ripening.

Control of the expression of genes associated with cell wall degradation is useful in controlling many plant processes, including fruit ripening. Characterization and cloning of such genes from many agronomically important plants is lacking in the prior art. The present invention addresses these and other needs.

SUMMARY OF THE INVENTION

The present invention provides isolated nucleic acid molecules comprising a strawberry Cel1 polynucleotide sequence. The polynucleotides of the invention can be identified by their ability to specifically hybridize to SEQ ID NO:1 under stringent conditions. The Cel1 polynucleotides of the invention are typically at least about 100 nucleotides in length. The Cel1 polynucleotides encode a polypeptide as shown in SEQ ID NO:2. A preferred Cel1 polynucleotide sequence is set forth in SEQ ID NO:1.

If transcription of the Cel1 polynucleotide is desired, the nucleic acid molecules of the invention may further comprise a plant promoter operably linked to the Cel1 polynucleotide. The plant promoter used is not critical to the invention and may be, for instance, a promoter that drives expression in fruit tissue. In some embodiments the Cel1 polynucleotide is linked to the promoter in an antisense orientation.

The invention also provides transgenic plants comprising an expression cassette containing a plant promoter operably linked to a heterologous Cel1 polynucleotides of the invention. The heterologous Cel1 polynucleotide may encode a Cel1 polypeptide, such as one shown in SEQ ID NO:2. Alternatively, the Cel1 polynucleotide may be linked to the promoter in an antisense orientation.

The invention further provides methods of modulating cell wall degradation in plants. The methods comprise introducing into the plant an expression cassette containing a plant promoter operably linked to a heterologous Cel1 polynucleotide. The heterologous Cel1 polynucleotide may be used to encode a Cel1 polypeptide or may be used to inhibit expression of an endogenous Cel1 polynucleotide. In these embodiments, the Cel1 polynucleotide may be linked to the promoter in a sense or antisense orientation. The expression cassette can be introduced into the plant using genetic engineering techniques or through a sexual cross.

Definitions

The phrase "nucleic acid sequence" refers to a single or double-stranded polymer of deoxyribonucleotide or ribonucleotide bases read from the 5' to the 3' end. It includes chromosomal DNA, self-replicating plasmids, infectious polymers of DNA or RNA and DNA or RNA that performs a primarily structural role. One of skill will understood that, unless noted otherwise, a disclosure of single strand of DNA sequence (e.g., as shown in the Sequence Listing) inherently includes the complementary strand, as well.

A "promoter" is defined as an array of nucleic acid control sequences that direct transcription of an operably linked nucleic acid. As used herein, a "plant promoter" is a promoter that functions in plants. Promoters include necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. A "constitutive" promoter is a promoter that is active under most environmental and developmental conditions. An "inducible" promoter is a promoter that is active under environmental or developmental regulation. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

The term "plant" includes whole plants, plant organs (e.g., leaves, stems, flowers, roots, etc.), seeds and plant cells and progeny of same. The class of plants which can be used in the method of the invention is generally as broad as the class of higher plants amenable to transformation techniques, including angiosperms (monocotyledonous and dicotyledonous plants), as well as gymnosperms. It includes plants of a variety of ploidy levels, including polyploid, diploid, haploid and hemizygous.

A polynucleotide sequence is "heterologous to" an organism or a second polynucleotide sequence if it originates from a foreign species, or, if from the same species, is modified from its original form. For example, a promoter operably linked to a heterologous coding sequence refers to a coding sequence from a species different from that from which the promoter was derived, or, if from the same species, a coding sequence which is different from any naturally occurring allelic variants.

A polynucleotide "exogenous to" an individual plant is a polynucleotide which is introduced into the plant by any means other than by a sexual cross. Examples of means by which this can be accomplished are described below, and include Agrobacterium-mediated transformation, biolistic methods, electroporation, and the like. Such a plant containing the exogenous nucleic acid is referred to here as an $R_1$ generation transgenic plant. Transgenic plants which arise from sexual cross or by selfing are descendants of such a plant.

A "Cel1 nucleic acid" or "Cel1 polynucleotide sequence" of the invention is a subsequence or full length polynucleotide sequence of a gene which encodes a polypeptide capable of cleaving β-1,4 glucan linkages and degrading carboxymethylcellulose. A Cel1 polynucleotide is typically at least about 30–40 nucleotides to about 2000 nucleotides in length. The nucleic acids contain coding sequence of from about 100 to about 2000 nucleotides, often from about 500 to about 1500 nucleotides in length.

In the case of both expression of transgenes and inhibition of endogenous genes (e.g., by antisense, or sense suppression) one of skill will recognize that the inserted polynucleotide sequence need not be identical, but may be only "substantially identical" to a sequence of the gene from which it was derived. As explained below, these substantially identical variants are specifically covered by the term Cel1 nucleic acid.

In the case where the inserted polynucleotide sequence is transcribed and translated to produce a functional polypeptide, one of skill will recognize that because of codon degeneracy a number of polynucleotide sequences will encode the same polypeptide. These variants are specifically covered by the terms "Cel1 nucleic acid". In addition, the term specifically includes those sequences substantially identical (determined as described below) with an Cel1 polynucleotide sequence disclosed here and that encode polypeptides that are either mutants of wild type Cel1 polypeptides or retain the function of the Cel1 polypeptide (e.g., resulting from conservative substitutions of amino acids in the Cel1 polypeptide). In addition, variants can be those that encode dominant negative mutants as described below.

Two nucleic acid sequences or polypeptides are said to be "identical" if the sequence of nucleotides or amino acid residues, respectively, in the two sequences is the same when aligned for maximum correspondence as described below. The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence over a comparison window, as measured using one of the following sequence comparison algorithms or by manual alignment and visual inspection. When percentage of sequence identity is used in reference to proteins or peptides, it is recognized that residue positions that are not identical often differ by conservative amino acid substitutions, where amino acids residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated according to, e.g., the algorithm of Meyers & Miller, *Computer Applic. Biol. Sci.* 4:11–17 (1988) e.g., as implemented in the program PC/GENE (Intelligenetics, Mountain View, Calif., USA).

The phrase "substantially identical," in the context of two nucleic acids or polypeptides, refers to sequences or subsequences that have at least 60%, preferably 80%, most preferably 90–95% nucleotide or amino acid residue identity when aligned for maximum correspondence over a comparison window as measured using one of the following sequence comparison algorithms or by manual alignment and visual inspection. This definition also refers to the complement of a test sequence, which has substantial sequence or subsequence complementarity when the test sequence has substantial identity to a reference sequence.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection.

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle, *J. Mol. Evol.* 35:351–360 (1987). The method used is similar to the method described by Higgins & Sharp, *CABIOS* 5:151–153 (1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. For example, a reference sequence can be compared to other test sequences to determine the percent sequence identity relationship using the following parameters: default gap weight (3.00), default gap length weight (0.10), and weighted end gaps.

Another example of algorithm that is suitable for determining percent sequence identity and sequence similarity is the BLAST algorithm, which is described in Altschul et al., *J. Mol. Biol.* 215:403–410 (1990). Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are extended in both directions along each sequence for as far as the cumulative alignment score can be increased. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLAST program uses as defaults a wordlength (W) of 11, the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, *Proc. Natl. Acad. Sci. USA* 90:5873–5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is speciCel1d by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art.

The following six groups each contain amino acids that are conservative substitutions for one another:
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).
(see, e.g., Creighton, Proteins (1984)).

An indication that two nucleic acid sequences or polypeptides are substantially identical is that the polypeptide encoded by the first nucleic acid is immunologically cross reactive with the antibodies raised against the polypeptide encoded by the second nucleic acid. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, highly stringent conditions are selected to be about 5–10° C. lower than the thermal melting point ($T_m$) for the specific sequence at a defined ionic strength pH. Low stringency conditions are generally selected to be about 15–30° C. below the $T_m$. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, preferably 10 time background hybridization.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cased, the nucleic acids typically hybridize under moderately stringent hybridization conditions.

In the present invention, genomic DNA or cDNA comprising Cel1 nucleic acids of the invention can be indentified in standard Southern blots under stringent conditions using the nucleic acid sequences disclosed here. For the purposes of this disclosure, suitable stringent conditions for such hybridizations are those which include a hybridization in a buffer of 40% formamide, 1 M NaCl, 1% SDS at 37° C., for 12 hours, and at least one wash in 0. 1X SSC, 0.1% (w/v) SDS at a temperature of at least about 50° C., usually about 55° C., or preferably 65° C., for 20 minutes, or equivalent conditions. A positive hybridization is at least twice background. Those of ordinary skill will readily recognize that alternative hybridization and wash conditions can be utilized to provide conditions of similar stringency.

A further indication that two polynucleotides are substantially identical is if the reference sequence, amplified by a pair of oligonucleotide primers, can then be used as a probe under stringent hybridization conditions to isolate the test sequence from a cDNA or genomic library, or to identify the test sequence in, e.g., a northern or Southern blot.

DESCRIPTION OF THE PREFERRED EMBODIMENTS

The present invention is directed to new polynucleotides useful in controlling cell wall degradation, particularly in strawberry. The polynucleotides are conveniently used to inhibit fruit softening. In these methods, vector containing an expression cassette having a plant promoter operably linked to a Cel1 polynucleotide (in the sense or antisense orientation) is introduced into a plant cell. Control of fruit softening during the ripening process is of tremendous economic importance. Control of fruit ripening may also improve fruit quality by increasing pathogen resistance. These properties allow for longer shelf and shipping life of the strawberry fruit.

Isolation of Cel1 Nucleic Acids

Generally, the nomenclature and the laboratory procedures in recombinant DNA technology described below are those well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturer's specifications. These techniques and various other techniques are generally performed according to Sambrook et al., *Molecular Cloning—A Laboratory Manual*, Cold Spring Harbor Laboratory, Cold Spring Harbor, N.Y., (1989).

The isolation of Cel1 nucleic acids may be accomplished by a number of techniques. For instance, oligonucleotide probes based on the sequences disclosed here can be used to identify the desired gene in a cDNA or genomic DNA library. To construct genomic libraries, large segments of genomic DNA are generated by random fragmentation, e.g. using restriction endonucleases, and are ligated with vector DNA to form concatemers that can be packaged into the appropriate vector. To prepare a cDNA library, MRNA is isolated from the desired organ, such as fruit, and a cDNA library which contains the Cel1 gene transcript is prepared from the MRNA. Alternatively, cDNA may be prepared from mRNA extracted from other tissues in which Cel1 genes or homologs are expressed.

The cDNA or genomic library can then be screened using a probe based upon the sequence of a cloned Cel1 gene disclosed here. Probes may be used to hybridize with genomic DNA or cDNA sequences to isolate homologous genes in the same or different plant species. Alternatively, antibodies raised against an Cel1 polypeptide can be used to screen an MRNA expression library.

Alternatively, the nucleic acids of interest can be amplified from nucleic acid samples using amplification techniques. For instance, polymerase chain reaction (PCR) technology can be used to amplify the sequences of the Cel1 genes directly from genomic DNA, from cDNA, from genomic libraries or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes. For a general overview of PCR see *PCR Protocols: A Guide to Methods and Applications*. (Innis, M, Gelfand, D., Sninsky, J. and White, T., eds.), Academic Press, San Diego (1990).

Appropriate primers and probes for identifying Cel1 sequences from plant tissues are generated from comparisons of the sequences provided here with other glucanase genes. For instance, Cel11 can be compared to the other glucanase genes described in the prior art. Using these techniques, one of skill can identify conserved regions in the nucleic acids disclosed here to prepare the appropriate primer and probe sequences. Primers that specifically hybridize to conserved regions in Cel1 genes can be used to amplify sequences from widely divergent plant species.

Standard nucleic acid hybridization techniques using the conditions disclosed above can then be used to identify full length cDNA or genomic clones.

Control of Cel1 Activity or Gene Expression

As noted above, since Cel1 genes are involved in cell wall degradation, controlling Cel1 activity or gene expression is useful in fruit softening and other processes One of skill will recognize that a number of methods can be used to modulate Cel1 activity or gene expression. Cel1 activity can be modulated in the plant cell at the gene, transcriptional, posttranscriptional, translational, or posttranslational, levels. Techniques for modulating Cel1 activity at each of these levels are generally well known to one of skill and are discussed briefly below.

Methods for introducing genetic mutations into plant genes are well known. For instance, seeds or other plant material can be treated with a mutagenic chemical substance, according to standard techniques. Such chemical substances include, but are not limited to, the following: diethyl sulfate, ethylene imine, ethyl methanesulfonate and N-nitroso-N-ethylurea. Alternatively, ionizing radiation from sources such as, for example, X-rays or gamma rays can be used.

Gene expression can be inactivated using recombinant DNA techniques by transforming plant cells with constructs comprising transposons or T-DNA sequences. Cel1 mutants prepared by these methods are identified according to standard techniques. For instance, mutants can be detected by PCR or by detecting the presence or absence of Cel1 mRNA, e.g., by Northern blots. Mutants can also be selected by assaying for decreased cell wall degradation.

The isolated nucleic acid sequences prepared as described herein, can also be used in a number of techniques to control endogenous Cel1 gene expression at various levels. Subsequences from the sequences disclosed here can be used to control, transcription, RNA accumulation, translation, and the like.

A number of methods can be used to inhibit gene expression in plants. For instance, antisense technology can be conveniently used. To accomplish this, a nucleic acid segment from the desired gene is cloned and operably linked to a promoter such that the antisense strand of RNA will be transcribed. The construct is then transformed into plants and the antisense strand of RNA is produced. In plant cells, it has been suggested that antisense suppression can act at all levels of gene regulation including suppression of RNA translation (see, Bourque *Plant Sci. (Limerick)* 105:125–149 (1995); Pantopoulos In Progress in Nucleic Acid Research and Molecular Biology, Vol. 48. Cohn, W. E. and K. Moldave (Ed.). Academic Press, Inc.: San Diego, Calif., USA; London, England, UK. p. 181–238; Heiser et al. *Plant Sci. (Shannon)* 127:61–69 (1997)) and by preventing the accumulation of MRNA which encodes the protein of interest, (see, Baulcombe *Plant Mol. Bio.* 32:79–88 (1996); Prins and Goldbach *Arch. Virol.* 141:2259–2276 (1996); Metzlaff et al.*Cell* 88:845–854 (1997), Sheehy et al., *Proc. Nat. Acad. Sci. USA*, 85:8805–8809 (1988), and Hiatt et al., U.S. Pat. No. 4,801,340).

The nucleic acid segment to be introduced generally will be substantially identical to at least a portion of the endogenous Cel1 gene or genes to be repressed. The sequence, however, need not be perfectly identical to inhibit expression. The vectors of the present invention can be designed such that the inhibitory effect applies to other genes within a family of genes exhibiting homology or substantial homology to the target gene.

For antisense suppression, the introduced sequence also need not be full length relative to either the primary transcription product or fully processed mRNA. Generally, higher homology can be used to compensate for the use of a shorter sequence. Furthermore, the introduced sequence need not have the same intron or exon pattern, and homology of non-coding segments may be equally effective. Normally, a sequence of between about 30 or 40 nucleotides and about full length nucleotides should be used, though a sequence of at least about 100 nucleotides is preferred, a sequence of at least about 200 nucleotides is more preferred, and a sequence of about 500 to about 1700 nucleotides is especially preferred.

Another method of suppression is sense suppression. Introduction of nucleic acid configured in the sense orientation has been recently shown to be an effective means by which to block the transcription of target genes. For an example of the use of this method to modulate expression of endogenous genes (see, Assaad et al. *Plant Mol. Bio.*

22:1067–1085 (1993); Flavell *Proc. Natl. Acad. Sci. USA* 91:3490–3496 (1994); Stam et al. *Annals Bot.* 79:3–12 (1997); Napoli et al., *The Plant Cell* 2:279–289 (1990); and U.S. Pat. Nos. 5,034,323, 5,231,020, and 5,283,184).

The suppressive effect may occur where the introduced sequence contains no coding sequence per se, but only intron or untranslated sequences homologous to sequences present in the primary transcript of the endogenous sequence. The introduced sequence generally will be substantially identical to the endogenous sequence intended to be repressed. This minimal identity will typically be greater than about 65%, but a higher identity might exert a more effective repression of expression of the endogenous sequences. Substantially greater identity of more than about 80% is preferred, though about 95% to absolute identity would be most preferred. As with antisense regulation, the effect should apply to any other proteins within a similar family of genes exhibiting homology or substantial homology.

For sense suppression, the introduced sequence, needing less than absolute identity, also need not be full length, relative to either the primary transcription product or fully processed mRNA. This may be preferred to avoid concurrent production of some plants which are overexpressers. A higher identity in a shorter than full length sequence compensates for a longer, less identical sequence. Furthermore, the introduced sequence need not have the same intron or exon pattern, and identity of non-coding segments will be equally effective. Normally, a sequence of the size ranges noted above for antisense regulation is used. In addition, the same gene regions noted for antisense regulation can be targeted using cosuppression technologies.

A number of gene regions can be targeted to suppress Cel1 gene expression. The targets can include, for instance, the coding regions, introns, sequences from exon/intron junctions, 5' or 3' untranslated regions, and the like. In some embodiments, the constructs can be designed to eliminate the ability of regulatory proteins to bind to Cel1 gene sequences that are required for its cell- and/or tissue-specific expression. Such transcriptional regulatory sequences can be located either 5'-, 3'-, or within the coding region of the gene and can be either promote (positive regulatory element) or repress (negative regulatory element) gene transcription. These sequences can be identified using standard deletion analysis, well known to those of skill in the art. Once the sequences are identified, a construct targeting these sequences is introduced into plants to control gene transcription.

Oligonucleotide-based triple-helix formation can be used to disrupt Cel1 gene expression. Triplex DNA can inhibit DNA transcription and replication, generate site-specific mutations, cleave DNA, and induce homologous recombination (see, e.g., Havre and Glazer *J. Virology* 67:7324–7331 (1993); Scanlon et al. FASEB J. 9:1288–1296 (1995); Giovannangeli et al. *Biochemistry* 35:10539–10548 (1996); Chan and Glazer *J. Mol. Medicine (Berlin)* 75:267–282 (1997)). Triple helix DNAs can be used to target the same sequences indentified for antisense regulation.

Catalytic RNA molecules or ribozymes can also be used to inhibit expression of Cel1 genes. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA-cleaving activity upon them, thereby increasing the activity of the constructs. Thus, ribozymes can be used to target the same sequences indentified for antisense regulation.

A number of classes of ribozymes have been identified. One class of ribozymes is derived from a number of small circular RNAs which are capable of self-cleavage and replication in plants. The RNAs replicate either alone (viroid RNAs) or with a helper virus (satellite RNAs). Examples include RNAs from avocado sunblotch viroid and the satellite RNAs from tobacco ringspot virus, lucerne transient streak virus, velvet tobacco mottle virus, solanum nodiflorum mottle virus and subterranean clover mottle virus. The design and use of target RNA-specific ribozymes is described in Zhao and Pick *Nature* 365:448–451 (1993); Eastham and Ahlering *J. Urology* 156:1186–1188 (1996); Sokol and Murray *Transgenic Res.* 5:363–371 (1996); Sun et al. *Mol. Biotechnology* 7:241–251 (1997); and Haseloff et al. *Nature,* 334:585–591 (1988).

Alternatively, Cel1 activity may be modulated by eliminating the proteins that are required for Cel1 cell-specific gene expression. Thus, expression of regulatory proteins and/or the sequences that control Cel1 gene expression can be modulated using the methods described here.

Use of Nucleic Acids of the Invention to Enhance Cel1 Gene Expression

Isolated sequences prepared as described herein can also be used to introduce expression of a particular Cel1 nucleic acid to enhance or increase endogenous gene expression. Enhanced expression can therefore be used to increase cell wall degradation. For example, enhanced expression of Cel1 can benefit production of processed products such as jams and preserves. Enhanced expression of Cel1 would also benefit an overly firm cultivar. Where overexpression of a gene is desired, the desired gene from a different species may be used to decrease potential sense suppression effects.

One of skill will recognize that the polypeptides encoded by the genes of the invention, like other proteins, have different domains which perform different functions. Thus, the gene sequences need not be full length, so long as the desired functional domain of the protein is expressed.

Modified protein chains can also be readily designed utilizing various recombinant DNA techniques well known to those skilled in the art and described in detail, below. For example, the chains can vary from the naturally occurring sequence at the primary structure level by amino acid substitutions, additions, deletions, and the like. These modifications can be used in a number of combinations to produce the final modified protein chain.

Preparation of Recombinant Vectors

To use isolated sequences in the above techniques, recombinant DNA vectors suitable for transformation of plant cells are prepared. Techniques for transforming a wide variety of higher plant species are well known and described in the technical and scientific literature. See, for example, Weising et al. *Ann. Rev. Genet.* 22:421–477 (1988). A DNA sequence coding for the desired polypeptide, for example a cDNA sequence encoding a full length protein, will preferably be combined with transcriptional and translational initiation regulatory sequences which will direct the transcription of the sequence from the gene in the intended tissues of the transformed plant.

For example, for overexpression, a plant promoter fragment may be employed which will direct expression of the gene in all tissues of a regenerated plant. Such promoters are referred to herein as "constitutive" promoters and are active under most environmental conditions and states of development or cell differentiation. Examples of constitutive promoters include the cauliflower mosaic virus (CaMV) 35S transcription initiation region, the 1'- or 2'- promoter derived from T-DNA of *Agrobacterium tumafaciens*, and other transcription initiation regions from various plant genes known to those of skill. Such genes include for example, ACT11 from Arabidopsis (Huang et al. *Plant Mol. Biol.* 33:125–139 (1996)), Cat3 from Arabidopsis (GenBank No. U43147, Zhong et al., *Mol. Gen. Genet.* 251:196–203 (1996)), the gene encoding stearoyl-acyl carrier protein desaturase from *Brassica napus* (Genbank No. X74782, Solocombe et al. *Plant Physiol.* 104:1167–1176 (1994)), GPc1 from maize (GenBank No. X15596, Martinez et al. *J. Mol. Biol* 208:551–565 (1989)), and Gpc2 from maize (GenBank No. U45855, Manjunath et al., *Plant Mol. Biol.* 33:97–112 (1997)).

Alternatively, the plant promoter may direct expression of the Cel1 nucleic acid in a specific tissue or may be otherwise under more precise environmental or developmental control. Examples of environmental conditions that may effect transcription by inducible promoters include anaerobic conditions, elevated temperature, or the presence of light. Such promoters are referred to here as "inducible" or "tissue-specific" promoters. One of skill will recognize that a tissue-specific promoter may drive expression of operably linked sequences in tissues other than the target tissue. Thus, as used herein a tissue-specific promoter is one that drives expression preferentially in the target tissue, but may also lead to some expression in other tissues as well.

Examples of promoters under developmental control include promoters that initiate transcription only (or primarily only) in certain tissues, such as fruit, seeds, or flowers. Promoters that direct expression of nucleic acids in fruit are particularly useful in the present invention. Examples of promoters useful for this purpose include the tomato E8 promoter, the tomato polygalacturonase promoter, and pepper Group 2 promoters (see, e.g., U.S. Ser. No. 08/761,549 (now U.S. Pat. No. 5,981,727) and U.S. Pat. No. 5,608,144).

If proper polypeptide expression is desired, a polyadenylation region at the 3'-end of the coding region should be included. The polyadenylation region can be derived from the natural gene, from a variety of other plant genes, or from T-DNA.

The vector comprising the sequences (e.g., promoters or coding regions) from genes of the invention will typically comprise a marker gene which confers a selectable phenotype on plant cells. For example, the marker may encode biocide resistance, particularly antibiotic resistance, such as resistance to kanamycin, G418, bleomycin, hygromycin, or herbicide resistance, such as resistance to chlorosulfuron or Basta.

Production of Transgenic Plants

DNA constructs of the invention may be introduced into the genome of the desired plant host by a variety of conventional techniques. For example, the DNA construct may be introduced directly into the genomic DNA of the plant cell using techniques such as electroporation and microinjection of plant cell protoplasts, or the DNA constructs can be introduced directly to plant tissue using ballistic methods, such as DNA particle bombardment.

Microinjection techniques are known in the art and well described in the scientific and patent literature. The introduction of DNA constructs using polyethylene glycol precipitation is described in Paszkowski et al. *Embo J.* 3:2717–2722 (1984). Electroporation techniques are described in Fromm et al. *Proc. Natl. Acad. Sci. USA* 82:5824 (1985). Ballistic transformation techniques are described in Klein et al. *Nature* 327:70–73 (1987).

Alternatively, the DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria. *Agrobacterium tumefaciens*-mediated transformation techniques, including disarming and use of binary vectors, are well described in the scientific literature. See, for example Horsch et al. *Science* 233:496–498 (1984), and Fraley et al. *Proc. Natl. Acad. Sci. USA* 80:4803 (1983).

Transformed plant cells which are derived by any of the above transformation techniques can be cultured to regenerate a whole plant which possesses the transformed genotype and thus the desired phenotype such as increased seed mass. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Evans et al., *Protoplasts Isolation and Culture, Handbook of Plant Cell Culture*, pp. 124–176, MacMillilan Publishing Company, New York, 1983; and Binding, *Regeneration of Plants, Plant Protoplasts*, pp. 21–73, CRC Press, Boca Raton, 1985. Regeneration can also be obtained from plant callus, explants, organs, or parts thereof. Such regeneration techniques are described generally in Klee et al. *Ann. Rev. of Plant Phys.* 38:467–486 (1987).

The nucleic acids of the invention can be used to confer desired traits on essentially any plant. Thus, the invention has use over a broad range of plants, including species from the genera Anacardium, Arachis, Asparagus, Atropa, Avena, Brassica, Citrus, Citrullus, Capsicum, Carthamus, Cocos, Coffea, Cucumis, Cucurbita, Daucus, Elaeis, Fragaria, Glycine, Gossypium, Helianthus, Heterocallis, Hordeum, Hyoscyamus, Lactuca, Linum, Lolium, Lupinus, Lycopersicon, Malus, Manihot, Majorana, Medicago, Nicotiana, Olea, Oryza, Panieum, Pannesetum, Persea, Phaseolus, Pistachia, Pisum, Pyrus, Prunus, Raphanus, Ricinus, Secale, Senecio, Sinapis, Solanum, Sorghum, Theobromus, Trigonella, Triticum, Vicia, Vitis, Vigna, and Zea.

One of skill will recognize that after the expression cassette is stably incorporated in transgenic plants and confirmed to be operable, it can be introduced into other plants by sexual crossing. Any of a number of standard breeding techniques can be used, depending upon the species to be crossed.

Seed obtained from plants of the present invention can be analyzed according to well known procedures to identify plants with the desired trait. If antisense or other techniques are used to control Cel1 gene expression, Northern blot analysis can be used to screen for desired plants. In addition, decreased fruit softening can be detected. For instance, fruit softening in strawberries is typically measured using penetrometer analysis, Instron analysis, or stress-relaxation analysis.

The following Examples are offered by way of illustration, not limitation.

Example 1

This example describes the cloning of a strawberry Cel1 cDNA.

Materials and Methods

Plant Material

Strawberry plants (*Fragatia x ananassa* L. cv Chandler) were grown in three gallon plastic bags and irrigated with fertilized water daily. Greenhouse temperatures ranged from 22° C. during the day to 12° C. at night. To promote synchronous flowering, potted runners were subjected to one week of preconditioning at 10° C. during the day and 5° C. at night. This regime was immediately followed by three weeks of vernalization at −2°C.

Unless otherwise indicated, all analyses were conducted using tissue which was harvested directly into liquid nitrogen and stored at −80° C. Although there is variability between fruit, the average times taken for fruit to attain a specific stage of development in the ripening process, and their color readings, are as follows: small green (14 dpa, $a^*=-14.4\pm0.4$), large green (20 dpa, $a^*=-12.8\pm0.5$), small white (28 dpa, $a^*=-11.3\pm1.5$), large white (35 dpa, $a^*=-9.4\pm1.1$), turning (40 dpa, $a^*=1.7\pm8.1$), red ripe (45 dpa, $a^*=24.8\pm1.2$) and overripe (>55 dpa, $a^*=21.5\pm2.9$). Color readings were conducted with a Minolta model CR-300 colorimeter and are described by the $a^*$ value on the CIE $L^*a^*b^*$ scale, which is a measure of green (negative) to red (positive) reflectance of the visible spectrum. The standard reference for the $L^*a^*b$ color system has been established by CIE (1976) (Commission Internationale d'Eclairage) and is based on a measure of human sensitivity to color. Values given are means of at least four readings ±SD.

cDNA Cloning

The isolation of EGase cDNAs was conducted by screening a Uni-Zap XR cDNA library (Stratagene) constructed from red fruit poly(A)+mRNA. Hybridization conditions were empirically determined by probing replicate Northern blots of red fruit total RNA over a range of temperatures with end-labelled ($[\gamma-^{32}P]ATP$, >5000 Ci mmol$^{-1}$) degenerate oligonucleotides corresponding to domain CWERPEDM (SEQ ID NO:5). Hybridization at 55° C. in 7% (w/v) SDS, 0.25 M sodium phosphate (pH 7.4), 1 mM EDTA and I % (w/v) BSA (type V) provided the recognition of a single MRNA species of the appropriate size for EGase (~1.8 kb). Using these same conditions, library lifts were then hybridized and washed in 2X SSC (1X SSC is 0.15 M NaCl and 15 mM sodium citrate pH 7.0) and 0.1% (w/v) SDS at 55° C. Following the purification of phage from hybridizing plaques and the in vivo excision of cloned inserts into phagemids, doublestranded DNA minipreps were partially characterized by dideoxy sequencing (Sanger et al., *Proc Natl Acad Sci USA* 74:5463–5467 (1977)) and restriction endonuclease mapping.

Southern Blot Analysis

Strawberry genomic DNA was isolated using a small scale extraction procedure which employs urea as a denaturant (Greene et al., *Genetics* 138:1275–1285 (1994)). Contaminating pectins were removed by selective precipitation with 2-butoxyethanol (Sigma). DNA digestion, gel and electrophoresis conditions and probe hybridization conditions have been described elsewhere (Harpster et al., *Plant Mol Biol* 33:47–59 (1997)). High-stringency blot washes were done at 65° C. in 0. 1X SSC and 0.1% (w/v) SDS.

RNA Isolation and Expression Analysis

Total RNA was isolated from different tissues of strawberry plants using a hot borate/phenol method (Wan et al., *Anal Biochem* 223:7–12 (1994)) with several modifications. Strawberry tissue (1 to 2 g) was first ground to a fine powder in liquid nitrogen and then transferred to a 15 mL polypropylene tube containing 5 mL of borate extraction buffer (0.2 M borax, 30 mM EGTA, 1% (w/v) sodium deoxycholate, 1% (w/v) SDS and 10 mM DTT) adjusted to 85° C. The sample was vortexed for 10 s, after which an equal volume of phenol/chloroform/isoamyl alcohol (25:24:1, v/v/v) was added and the sample vortexed an additional 30 s. The sample was then transferred to a 15 mL Corex tube and centrifuged at 8000 rpm for 10 min at 4° C. After removal of the aqueous layer and reextraction with an equal volume of chloroform/isoamyl alcohol (24:1, v/v), the sample was centrifuged at 3000 rpm for 5 min and the aqueous layer transferred to a Corex tube containing an equal volume of 4 M lithium acetate. The sample was incubated at 4° C. overnight, centrifuged at 8000 rpm for 20 min and the supernatant discarded. To remove pigments, the pellet was resuspended in 0.5 mL of cold 2 M lithium acetate, transferred to a microphage tube and then repeatedly pelleted (14,000 rpm for 5 min at 4° C.) and resuspended in 2 M lithium acetate until the supernatant was clear of pigmentation (2X for fruit RNA and 3–4X for leaf RNA). Following the last precipitation, the pellet was resuspended in 0.3 mL of water with vigorous vortexing, adjusted to 0.2 M potassium acetate (pH 5.5) and vortexed for 20–30 s with an equal volume of phenol/chloroform/isoamyl alcohol. Finally, the sample was centrifuged (5 min at 4° C.), the aqueous layer transferred to a microphage tube containing 2.5 volumes of ethanol and the RNA precipitated. Yields of total RNA from leaf tissue are 600–1200 $\mu$g g$^{-1}$ gel fresh weight and 40–100 $\mu$g gel fresh weight for fruit tissue. Northern analysis was conducted as described elsewhere (Harpster et al., *Plant Mol Biol* 33:47–59 (1997)) and high-stringency blot washes were performed as described for Southern blots.

Hormone Treatment

Deachenation was conducted by removing the achenes from longitudinal halves of green/small white fruit (on the vine) with needle-nose watchmaker forceps. For hormone treatment, NAA was applied to longitudinal halves of similarly staged fruit (possessing achenes) at a concentration of 0.2 mM in a lanolin paste containing 1% (v/v) DMSO. Seven days following deachenation and auxin treatment, tissue encompassing the zone separating treated/untreated halves (I.E., deachenated/achenated and +NAA/−NAA) was discarded (slice of ~5 mm in thickness) and the remaining halves wiped clean of the lanolin, frozen separately and stored at −80° C. Color readings of the individual fruit halves on the $L^*a^*b^*$ scale were recorded as above.

Protein Extraction and CMCase Activity Measurements

Soluble protein extracts used for both CMCase activity measurements and analysis by SDS-PAGE were prepared from strawberry tissues by first grinding frozen samples to a fine powder in liquid nitrogen. The powders were then ground in a mortar and pestle to a thick slurry by the addition of cold 100% acetone, which was gravity filtered using Whatman #1 filter paper and extensively washed with acetone (50 mL g$^{-1}$ fresh weight of tissue) until the filtrates were clear of pigment. After air drying the retentates to a powder, samples were either frozen in liquid nitrogen and stored at −80° C. until further use or processed immediately. To extract soluble proteins, acetone powders were first ground in liquid nitrogen, and then ground further in extraction buffer (0.1 M sodium phosphate (pH 6.0), 9.2 mM borax, 13 mM boric acid, 5 mM EDTA, 5 mM DTT, 0.15 M NaCl, 0.5% Triton-X) containing a cocktail of proteinase inhibitors (see Harpster et al., 1997). The resultant slurry was centrifuged at 20,000 rpm (4° C.) for 15 min to remove insolubles and the supernatant assayed directly for relative CMCase activity by viscometry (Harpster et al., *Plant Mol Biol* 33:47–59 (1997)). For preparation of samples for electrophoresis, the protein concentration of supernatants was determined using the dye-binding method of Bradford (1977), after which the desired amount of protein was adjusted to 80% (v/v) acetone and incubated on ice for a minimum of 30 min. Samples were then centrifuged (14,000 rpm for 10 min at 4° C.) and the protein pellets dried and resuspended in sample loading buffer (20 mM Tris-Cl pH 6.8, 3% [w/v] SDS, 10% [v/v] glycerol and 0.01% [w/v] bromphenol blue) by boiling for 10 min. To prevent band smearing during electrophoresis, residual insolubles were removed from samples by centrifugation at 14,000 rpm for 10 min prior to loading. Molecular weight markers were purchased from BRL.

Antibody Preparation and Western Blot Analysis

Polyclonal antiserum was raised against strawberry EGase by popliteal lymph node injections of white New Zealand rabbits with a protein A/Cel1 fusion protein. The fusion consisted of a 1.53 kb NarI-HincII fragment containing a 189 bp deletion of the Cel1 ORF (deleting 63 amino acids at the amino terminus of Cel1 protein) and 224 bp of 3' untranslated sequence which was translationally fused to a protein A fusion protein vector (Harpster et al., *Plant Mol Biol* 33:47–59 (1997)). The resultant construct produces a fusion protein which is localized in inclusion bodies and inefficiently binds IgG-Sepharose (Pharmacia). Hence, partial purification of the fusion protein for antibody production was performed by preparative SDS-PAGE as previously described (Harpster et al., *Plant Mol Biol* 33:47–59 (1997)).

Western blot analysis of ripe fruit protein extracts was carried out as described in Taylor et al. (1987) and provided a complex of several cross-reacting polypeptide species, despite the observation that parallel blots treated with pre-immununue serum demonstrated an absence of background hybridization (data not shown). Previous work using antiserum raised against a ripening-related pepper EGase, PCEL1, suggests that the majority of these cross-reacting polypeptides are cell wall-associated proteins with shared antigenic epitopes (Harpster et al., *Plant Mol Biol* 33:47–59 (1997)). To enrich for antibodies specific to strawberry Cel1, contaminating antibodies were selectively removed by passing antiserum over an affinity column containing covalently coupled protein isolated from small green fruit tissue which shows an absence of Cel1 expression. This was accomplished by first desalting a soluble protein extract from small green fruit on a PD-10 column (Pharmacia) and then covalently coupling the protein to a HiTrap column according to manufacturer's instructions (Pharmacia). Finally, antiserum was loaded onto the column, which was sealed and incubated overnight at 10° C. Unbound antiserum was collected from the column according to the manufacturer's instructions and when used in subsequent Western blot analysis of fruit protein extracts showed the selective enrichment of a single 62 kD polypeptide species (FIG. 5).

Results

Isolation of EGase cDNAs from Strawberry and characterization of Encoded Protein Using degenerate oligonucleotides corresponding to a conserved amino acid domain shared by plant EGases (see Materials and Methods), 55 putative EGase cDNAs were identified in the screening of a phage cDNA library constructed from red fruit poly(A)+MRNA. As this library was not amplified and 80,000 plaques were screened, it is estimated that strawberry EGase expression accounts for 0.07% of poly(A)+mRNA isolated from red fruit. Plasmid cross-hybridization experiments employing all cDNA clones and dideoxy sequencing analysis at the 5' and 3' ends of a subset of these clones demonstrated that they were all derived from the expression of a single gene; designated strawberry Cel1 (SEQ ID NO:1). Analysis at the 5' end of the longest cDNA identified showed that it contained the entire ORF and 14 bases of sequence upstream of the presumptive ATG initiation codon. The 3' analysis of all cDNAs identified an untranslated region of approximately 260 bases and a minimum of three alternate, closely-spaced polyadenylation sites.

Translation of the ORF provides a predicted polypeptide of 496 amino acids ($M_r$ of 54,600), the identification of a putative signal sequence of 32 amino acids and a single N-glycosylation site (SEQ ID NO:2).

Genomic Southern Blot Analysis of Cel1

*Fragatia x ananassa* cv. Chandler is a highly cultivated octoploid variety which is the product of the hybridization of two diploid species, *F. chiloensis* and *F. virginiana* (Hancock et al. In J Janick, J N Moore, eds, Fruit Breeding. Vol. II. Vine and Small Fruits, John Wiley and Sons, Inc., New York, pp 419–470 (1996)). Genomic Southern blot analysis yields a complex banding pattern which does not provide an accurate assessment of gene copy number. Presumably, some of this complexity reflects allelic polymorphism which has become fixed over time due to vegetative propagation. In order to estimate the number of genes encoding Cel1, genomic DNA was analyzed from *F. vesca*, a diploid line. Based on the hybridization profile and the observation that all of the bands revealed in the digestion of *F. vesca* appear to be a subset of the bands provided by the digestion of *F. x ananassa*, strawberry Cel1 appears to be encoded by single gene. Although the Southern blot profiles of the two diploid parental lines were note analyzed, the complexity of the banding pattern for *F. x ananassa* is also consistent with each line having contributed a single, polymorphic allele of Cel1 in the original interspecific cross. The presence of faint bands in both blots may indicate the presence of highly diverged sequences which collectively comprise a small, multigene family for EGase in strawberry.

Expression of Cel1 in strawberry tissues

Northern blot analysis of total RNA isolated from developing fruit reveals Cel1 expression as a 1.8 kb transcript which is first detectable in small white fruit. Thereafter, transcript levels gradually increase as fruits enlarge and attain maximum size at the red ripe stage. In red ripe fruit, steady-state Cel1 MRNA levels are at their highest, and no significant change in expression levels is observed in fruit which has evident signs of deterioration (I.E., tissue rotting, liquefaction). Although the pattern of Cel1 mRNA accumulation presented here shows an abrupt increase in steady-state levels between large white and red ripe fruit, higher levels in large white fruit and a more gradual increase in transcript accumulation were occasionally observed. This suggests that the increase in Cel1 MnRNA abundance and the development of red coloration are not necessarily coupled. Autoradiograph exposure in excess of two weeks of the blot shown here reveals an apparent absence of Cel1 expression in developing green fruit.

The analysis of Cel1 transcript levels in other tissues of mature, flowering strawberry plants shows that Cel1 expression is restricted to developing fruit. No expression in leaves regardless of size and age, floral stem tissue, vegetative stem tissue, roots, the primary tissues of dissected flowers and callus was observed. The high-level expression observed in red fruit of the cv. Chandler does not appear to show any cultivar specificity, insofar as expression levels are comparably high in ripe fruit of the cv. Camarosa.

Auxin Effects on Cel1 Expression

As with other non-climacteric fruit, ethylene production levels in ripening strawberry are exceptionally low and have been reported to decrease on a per unit fresh weight basis when harvested fruit turn from white to red (Knee et al., *J Exp Bot* 28:377–39 (1977)). To investigate the role of auxin in Cel1 expression, three auxins were tested for their capacity to inhibit ripening; IAA and the two auxin analogues 2,4-D and NAA. Based on a demonstrable reduction in visible anthocyanin accumulation relative to control fruit, two readings ±SD. Color readings (a* on the CIE L*a*b* scale) are given on a green (negative) to red (positive) scale.

| Fruit number | Deachenation | | Auxin treatment | | | |
|---|---|---|---|---|---|---|
| | | | Control | | Auxin | |
| | +Achenes | −Achenes | Untreated | Lanolin | Untreated | Lanolin + NAA |
| Fruit 1 | 4.2 ± 4.3 | 18.4 ± 5.1 | 20.1 ± 1.3 | 15.7 ± 0.3 | 25.7 ± 1.7 | −4.6 ± 0.1 |
| Fruit 2 | −2.4 ± 4.0 | 20.7 ± 1.8 | 22.2 ± 3.5 | 17.6 ± 1.5 | 8.5 ± 2.3 | −5.4 ± 1.1 |

NAA was the most effective (>90% of treated fruit) in retarding ripening when applied to small white fruit on the vine, 2,4-D was marginally effective (<25% of treated fruit) and IAA performed poorly. Presumably, the higher frequency of fruit showing a substantial decrease in anthocyanin accumulation following NAA treatment is a consequence of enhanced hormone uptake and/or stability relative to 2,4-D and IAA-treated fruit.

To test whether Cel1 expression is affected by the removal of endogenous auxin, achenes were manually removed from the longitudinal halves of individual, small white fruit (on the vine), which were then harvested seven days later. Fruit treated in this manner show a dramatic increase in Cel1 transcript levels in the deachenated halves.

Furthermore, this is accompanied by an enrichment in anthocyanin levels in the deachenated halves as measured by colorimetry (Table 1). In conducting this experiment, any fruit which showed signs of an induced wound response were discarded. Wound responses were evident as extensive browning within the outer epidermal layers of the fruit tissue.

To further examine the effect of auxin on Cel1 expression, transcript levels were measured by Northern analysis in NAA-treated and control small white fruit. The results were obtained at seven days post-application, in which total RNA was isolated from the separately treated longitudinal halves of control fruit (+/− lanolin) and hormone-treated fruit (+/− lanolin and NAA). At this time, Cel1 mRNA levels are low to undetectable in fruit sectors treated with NAA and have accumulated to high levels in tissue lacking exogenous hormone treatment. This reduction in Cel1 steady-state transcript levels is correlated with an absence of anthocyanin pigment accumulation, whereas untreated halves show a reddening of tissue (Table 1).

As it is well established that achenes are a rich source of auxins, the concentration of which declines during strawberry fruit ripening (Dreher et al. *J. Plant Growth Regu.* 1:267–276 (1982); Given et al., *Planta* 174:402–406 (1988b)), these results provide corollary evidence that Cel1 expression is inhibited by auxins. Clearly, the removal of endogenous auxin through deachenation facilitates the premature initiation of the ripening program, which is accompanied by the accumulation of Cel1 MRNA.

Table I.

Color readings of longitudinal halves of whole fruit after deachenation and treatment with auxin. Whole fruit on the vine were either deachenated on one half and the other half left untreated, or one half of otherwise intact fruit was left untreated and the other half coated with lanolin alone or with lanolin containing 0.2 mM NAA. After seven days, fruit were harvested, dissected longitudinally and the untreated and treated halves analyzed separately. Two fruit per treatment were analyzed and each value shown is the mean of Cel1 Protein and EGase Activity in Mature Strawberry Plants Using polyclonal antiserum raised against a protein A/Cel1 fusion protein, Western analysis of high salt-soluble protein extracts prepared from a variety of strawberry tissues shows a major cross-reacting species of 62 kD which is restricted to those tissues demonstrating Cel1 expression. Whereas all fruit samples, excepting small green fruit, show comparable accumulation of this protein, there is a clear absence in all other tissues examined. The detection of a second cross-reacting polypeptide species of approximately 60 kD in fruit stems, leaf stems and leaves may indicate the presence of a highly diverged isoform which shares common antigenic epitopes with Cel1 protein. While these data suggest that the 62 kD polypeptide is encoded by the Cel1 locus, the molecular weight is significantly larger than what is predicted for the mature, processed protein (approximately 51 kD). There is, however, evidence for the post-translational modification of EGases (Bennett et al. *Plant Physiol* 81:830–835 (1986); Kanellis et al., *Plant Physiol* 98:530–53 (1992)). In efforts to account for this disparity, the affinity of Cel1 protein to conA-Sepharose was tested. No binding was detected; suggesting that it may not be a high glucose/mannose glycoprotein.

Although Cel1 protein accumulation is limited to ripening fruit beyond the green stage of development, CMCase activity measurements of protein extracts demonstrate that EGases are present in all the major tissues of strawberry. In leaves, the highest levels of CMCase activity was detected, but Cel1 protein, if present, is below the limit of detection by Western analysis. Relatively high levels of enzyme activity are also recorded for green fruit, leaf stems, flower stems, flowers and roots, all of which do not have detectable Cel1 protein. These data support the existence of a highly diverged EGase gene family, with Cel1 as the ripening-related member.

Discussion

This invention provide an isolated and characterized cDNA corresponding to a ripening-related EGase, Cel1, from strawberry. As observed for cell wall-localized EGases from a wide variety of plant species, the amino-terminal sequence (32 amino acids) is predominately hydrophobic and shows homology with eukaryotic signal sequences (von Heijne G *Nucleic Acids Res* 14:4683–4690 (1986)). Although the sequence alignment of all EGases to date reveals several conserved amino acid domains, it is becoming clear that amino acid sequence homology and phylogenetic similarity do not necessarily predict function.

Strawberry Cel1 MRNA appears early in fruit development at the small white stage and accumulates to maximal levels in full-sized red fruit. As shown in previous studies (Given et al., *J Plant Physiol* 133:25–30 (1988a); Abeles et al., *Scientia Hortic* 42:269–275 (1990)), the onset of fruit softening in strawberry begins during the white stage and slightly precedes the appearance of anthocyanin pigments. Thereafter, fruit progressively exhibit a loss of firmness which nears a maximum at the red stage. This association between strawberry Cel1 expression and fruit softening is further supported by the absence of Cel1 mRNA and Cel1 protein in other tissues.

While strawberry Cel1 may be the sole EGase expressed in ripening fruit (it was the only sequence identified amongst 55 independent cDNAs isolated from a red fruit library), CMCase activity measurements of protein extracts prepared from developing fruit and a variety of tissues indicate the expression of other EGase genes. In green fruit, Cel1 expression is undetectable, yet total CMCase activity is approximately 80% of levels measured in red fruit. Furthermore, high levels of activity are also detected in leaf and leaf stem, with lower levels measured in flowers, flower stems, roots and fruit stems. The Southern data indicates that strawberry EGase is encoded by a small gene family and it is likely that CMCase activities measured in different tissues reflects the expression of one, or more, differentially expressed members of the gene family. In tomato, in which EGases have been shown to be encoded by a divergent gene family, there are at least seven members, each with its own characteristic pattern of tissue-specific expression and regulation (Lashbrook et al., *Plant Cell* 6:1485–1493 (1994); Milligan et al., *Plant Mol Biol* 28:691–7111 (1995); del Campillo et al. *Plant Physiol* 111:813–820 (1996); Brummell et al. *Plant Mol Biol* 33:87–95 (1997*a*); Brummell et al. *Proc Natl Acad Sci USA* 94:4794–4799 (1997b); Catala et al., *Plant J* 12:417–426 (1997)).

The above examples are provided to illustrate the invention but not to limit its scope. Other variants of the invention will be readily apparent to one of ordinary skill in the art and are encompassed by the appended claims. All publications, patents, and patent applications cited herein are hereby incorporated by reference.

What is claimed is:

1. An isolated double-stranded nucleic acid molecule comprising a strawberry Cel1 polynucleotide sequence, which polynucleotide sequence comprises SEQ ID NO:1, and which when operably linked to a promoter such that a protein is expressed, the protein cleaves β-1,4 glucan linkages.

2. The isolated nucleic acid molecule of claim 1, wherein the Cel1 polynucleotide is SEQ ID NO:1.

3. The isolated nucleic acid molecule of claim 1, further comprising a plant promoter operably linked to the Cel1 polynucleotide.

4. The isolated nucleic acid molecule of claim 3, wherein the plant promoter is a fruit-specific promoter.

5. The isolated nucleic acid of claim 4, wherein the Cel1 polynucleotide is linked to the promoter in an antisense orientation.

6. An isolated double stranded nucleic acid molecule comprising a Cel1 polynucleotide sequence, which polynucleotide sequence encodes Cel1 polypeptide as shown in SEQ ID NO:2, and which when operably linked to a promoter such that a protein is expressed, the protein cleaves β-1,4 glucan linkages.

7. A transgenic plant comprising an expression cassette containing a plant promoter operably linked to a heterologous Cel1 polynucleotide of claim 1.

8. The transgenic plant of claim 7, wherein the heterologous Cel1 polynucleotide encodes a Cel1 polypeptide.

9. The transgenic plant of claim 8, wherein the Cel1 polypeptide is as shown in SEQ ID NO:2.

10. The transgenic plant of claim 7, wherein the heterologous Cel1 polynucleotide is linked to the promoter in an antisense orientation.

11. The transgenic plant of claim 7, wherein the plant promoter is a fruit-specific promoter.

12. The transgenic plant of claim 11, wherein the Cel1 gene is as shown in SEQ ID NO:1.

13. The transgenic plant of claim 7, wherein the plant is a strawberry plant.

14. A method of modulating cell wall degradation in a plant, the method comprising introducing into a plant cell an expression cassette containing a plant promoter operably linked to a heterologous double-stranded Cel1 polynucleotide comprising SEQ ID NO:1 and which when operably linked to a promoter such that a protein is expressed, the protein cleaves β-1,4 glucan linkages., and regenerating a plant from said plant cell that contains said expression cassette.

15. The method of claim 14, wherein the heterologous Cel1 polynucleotide encodes a Cel1 polypeptide.

16. The method of claim 15, wherein the Cel1 polypeptide has an amino acid sequence as shown in SEQ ID NO:2.

17. The method of claim 14, wherein the heterologous Cel1 polynucleotide inhibits expression of an endogenous Cel1 polynucleotide.

18. The method of claim 17, wherein the heterologous Cel1 polynucleotide is linked to the promoter in a sense orientation.

19. The method of claim 14, wherein the heterologous Cel1 polynucleotide is SEQ ID NO:1.

20. The method of claim 14, wherein the plant promoter is from a Cel1 gene.

21. The method of claim 14, wherein the plant cell is from a strawberry plant.

22. The method of claim 14, wherein the expression cassette is introduced into the plant cell through a sexual cross.

* * * * *

SEQUENCE LISTING

```
<160> NUMBER OF SEQ ID NOS: 3

<210> SEQ ID NO: 1
<211> LENGTH: 1763
<212> TYPE: DNA
<213> ORGANISM: Fragaria x ananassa
<220> FEATURE:
<221> NAME/KEY: CDS
<222> LOCATION: (15)..(1505)
<223> OTHER INFORMATION: strawberry Cel1, endo-1,4-beta-glucanase
      (EGase)
<220> FEATURE:
<221> NAME/KEY: sig_peptide
<222> LOCATION: (15)..(110)

<400> SEQUENCE: 1
aacgagagaa aaaa atg gcg cga aat ggc ctt tgc tta cct gga aat gtt        50
              Met Ala Arg Asn Gly Leu Cys Leu Pro Gly Asn Val
                1               5                   10 ccc gca ttt cgc gca aca ctc gtc ctc tcg ctg ctc ctg ctt ctc cag        98
Pro Ala Phe Arg Ala Thr Leu Val Leu Ser Leu Leu Leu Leu Leu Gln
            15                  20                  25 cca atc agc gcc ggc cac gac tac cac gac gcc ctc cgc aag agc atc       146
Pro Ile Ser Ala Gly His Asp Tyr His Asp Ala Leu Arg Lys Ser Ile
        30                  35                  40 ctc ttc ttc gaa ggc cag cgc tcc ggc aag ctc ccg ccc gat caa cgc       194
Leu Phe Phe Glu Gly Gln Arg Ser Gly Lys Leu Pro Pro Asp Gln Arg
 45                  50                  55                  60 ctc aaa tgg cgc cgc gac tcc gca ttg cac gac ggc tcc acc gcc ggc       242
Leu Lys Trp Arg Arg Asp Ser Ala Leu His Asp Gly Ser Thr Ala Gly
                 65                  70                  75 gta gac tta acc ggc ggc tac tac gac gcc ggc gac aac gtg aag ttc       290
Val Asp Leu Thr Gly Gly Tyr Tyr Asp Ala Gly Asp Asn Val Lys Phe
             80                  85                  90 ggg ttt ccg atg gcg ttc acg acc act ctg ctg gcg tgg agc att ata       338
Gly Phe Pro Met Ala Phe Thr Thr Thr Leu Leu Ala Trp Ser Ile Ile
         95                 100                 105 gac ttc ggg cgg gtc atg ggg acg gag cag agg aac gcc gtc aag gcc       386
Asp Phe Gly Arg Val Met Gly Thr Glu Gln Arg Asn Ala Val Lys Ala
        110                 115                 120 tta cgg tgg ggg aca gac tac ctt ctg aag gcg acg gcg gtt cct ggc       434
Leu Arg Trp Gly Thr Asp Tyr Leu Leu Lys Ala Thr Ala Val Pro Gly
```

```
125                  130                  135                  140
gtc gtc ttc gtc caa gtc ggc gac cct tac tcc gac cac aac tgc tgg        482
Val Val Phe Val Gln Val Gly Asp Pro Tyr Ser Asp His Asn Cys Trp
                145                  150                  155 gag agg ccc gaa gac atg gac aca cgc cgc acg gtg tac aaa atc gac        530
Glu Arg Pro Glu Asp Met Asp Thr Arg Arg Thr Val Tyr Lys Ile Asp
                160                  165                  170 cac aac aac ccg gga tcc gac gtg gca gga gaa acc gcc gcc gcg ctc        578
His Asn Asn Pro Gly Ser Asp Val Ala Gly Glu Thr Ala Ala Ala Leu
                175                  180                  185 gcc gct gcc tcc atc gtt ttc agg tca cat gac ccc gct tac tcg aga        626
Ala Ala Ala Ser Ile Val Phe Arg Ser His Asp Pro Ala Tyr Ser Arg
        190                  195                  200 ctg ctt ctc aat cga gcc gtt agg gtt ttc gag ttc gct gat acc cac        674
Leu Leu Leu Asn Arg Ala Val Arg Val Phe Glu Phe Ala Asp Thr His
205                  210                  215                  220 cgc ggc ggc tac agc tcc agc ctc aaa aac gcc gtg tgc cct ttt tac        722
Arg Gly Gly Tyr Ser Ser Ser Leu Lys Asn Ala Val Cys Pro Phe Tyr
                225                  230                  235 tgc gac gtg aac ggc ttc cag gat gag tta ttg tgg gga gca gcg tgg        770
Cys Asp Val Asn Gly Phe Gln Asp Glu Leu Leu Trp Gly Ala Ala Trp
                240                  245                  250 ttg cac aag gcg tcg aga agg cgg cag tac aga gaa tac ata gtg aga        818
Leu His Lys Ala Ser Arg Arg Arg Gln Tyr Arg Glu Tyr Ile Val Arg
                255                  260                  265 aac gag gtc gtt ttg aga gct gga gat acc att aac gag ttt ggt tgg        866
Asn Glu Val Val Leu Arg Ala Gly Asp Thr Ile Asn Glu Phe Gly Trp
270                  275                  280 gat aac aag cat gct ggg att aat att ctc att tct aag gaa gtg ctt        914
Asp Asn Lys His Ala Gly Ile Asn Ile Leu Ile Ser Lys Glu Val Leu
285                  290                  295                  300 atg gga aaa gca gat tat ttc gaa tct ttc aag caa aat gca gat gga        962
Met Gly Lys Ala Asp Tyr Phe Glu Ser Phe Lys Gln Asn Ala Asp Gly
                305                  310                  315 ttt ata tgc tct gtt ttg cct gga ctt gcc cat acc caa gtc caa tat       1010
Phe Ile Cys Ser Val Leu Pro Gly Leu Ala His Thr Gln Val Gln Tyr
                320                  325                  330 tct cca ggt ggt ttg atc ttc aag cct gga ggg agt aac atg cag cat       1058
Ser Pro Gly Gly Leu Ile Phe Lys Pro Gly Gly Ser Asn Met Gln His
                335                  340                  345 gta act tcg ctc tcg ttc cta ctt ttg act tat tcc aac tat cta agc       1106
Val Thr Ser Leu Ser Phe Leu Leu Leu Thr Tyr Ser Asn Tyr Leu Ser
        350                  355                  360 cac gcc aat aag aac gtg ccg tgt ggc atg acc tcc gcc tcc ccg gcc       1154
His Ala Asn Lys Asn Val Pro Cys Gly Met Thr Ser Ala Ser Pro Ala
365                  370                  375                  380 ttc ctc aaa caa ttg gct aaa cgc cag gtg gat tac att ttg ggt gac       1202
Phe Leu Lys Gln Leu Ala Lys Arg Gln Val Asp Tyr Ile Leu Gly Asp
                385                  390                  395 aat cca tta aga atg tct tac atg gtt gga tat ggg ccg cgt tac ccg       1250
Asn Pro Leu Arg Met Ser Tyr Met Val Gly Tyr Gly Pro Arg Tyr Pro
                400                  405                  410 cag agg att cac cac agg ggc agc tca ctt cca tcg gtg cag gcc cat       1298
Gln Arg Ile His His Arg Gly Ser Ser Leu Pro Ser Val Gln Ala His
                415                  420                  425 ccg gcc cgt atc gga tgc aaa gcc ggt tct cgc tat ttt atg agt cca       1346
Pro Ala Arg Ile Gly Cys Lys Ala Gly Ser Arg Tyr Phe Met Ser Pro
        430                  435                  440 aat cca aac ccg aat aaa cta gtt ggg gcg gtt gtc ggc gga ccc aat       1394
```

-continued

```
Asn Pro Asn Pro Asn Lys Leu Val Gly Ala Val Val Gly Gly Pro Asn
445                 450                 455                 460 agc tcg gat gca ttt cca gac tcg agg cct tac ttt caa gag tct gag      1442
Ser Ser Asp Ala Phe Pro Asp Ser Arg Pro Tyr Phe Gln Glu Ser Glu
            465                 470                 475 ccc acg acg tac ata aat gcg ccg ctt gtg ggc cta ctt tcg tat ttt      1490
Pro Thr Thr Tyr Ile Asn Ala Pro Leu Val Gly Leu Leu Ser Tyr Phe
            480                 485                 490 gca gcc cat tac tgattctcga agtgtaaaca gtgaatgaga atttgtagtg          1542
Ala Ala His Tyr
            495 gtgcgccaat agtcacccac caatccccca ctctaccaat tgttgttcct tgtaaggttc    1602 taattgttaa tttctatcaa tgaagtcatg aagaaagaaa atgggccagg cttagttatg    1662 caatttagtc tcaaaagccc gactgatgtt gcttttgaga ggttctagtt gtaacaatat    1722 ttttgtcaac gaagaaagaa aatgggccaa gctagttttg t                        1763
```

<210> SEQ ID NO: 2
<211> LENGTH: 496
<212> TYPE: PRT
<213> ORGANISM: Fragaria x ananassa

<400> SEQUENCE: 2

```
Met Ala Arg Asn Gly Leu Cys Leu Pro Gly Asn Val Pro Ala Phe Arg
  1               5                  10                  15

Ala Thr Leu Val Leu Ser Leu Leu Leu Leu Gln Pro Ile Ser Ala
                 20                  25                  30

Gly His Asp Tyr His Asp Ala Leu Arg Lys Ser Ile Leu Phe Phe Glu
             35                  40                  45

Gly Gln Arg Ser Gly Lys Leu Pro Pro Asp Gln Arg Leu Lys Trp Arg
     50                  55                  60

Arg Asp Ser Ala Leu His Asp Gly Ser Thr Ala Gly Val Asp Leu Thr
 65                  70                  75                  80

Gly Gly Tyr Tyr Asp Ala Gly Asp Asn Val Lys Phe Gly Phe Pro Met
                 85                  90                  95

Ala Phe Thr Thr Thr Leu Leu Ala Trp Ser Ile Ile Asp Phe Gly Arg
            100                 105                 110

Val Met Gly Thr Glu Gln Arg Asn Ala Val Lys Ala Leu Arg Trp Gly
            115                 120                 125

Thr Asp Tyr Leu Leu Lys Ala Thr Ala Val Pro Gly Val Val Phe Val
        130                 135                 140

Gln Val Gly Asp Pro Tyr Ser Asp His Asn Cys Trp Glu Arg Pro Glu
145                 150                 155                 160

Asp Met Asp Thr Arg Arg Thr Val Tyr Lys Ile Asp His Asn Asn Pro
                165                 170                 175

Gly Ser Asp Val Ala Gly Glu Thr Ala Ala Leu Ala Ala Ala Ser
            180                 185                 190

Ile Val Phe Arg Ser His Asp Pro Ala Tyr Ser Arg Leu Leu Leu Asn
        195                 200                 205

Arg Ala Val Arg Val Phe Glu Phe Ala Asp Thr His Arg Gly Gly Tyr
    210                 215                 220

Ser Ser Ser Leu Lys Asn Ala Val Cys Pro Phe Tyr Cys Asp Val Asn
225                 230                 235                 240

Gly Phe Gln Asp Glu Leu Leu Trp Gly Ala Ala Trp Leu His Lys Ala
                245                 250                 255
```

```
                                    -continued

Ser Arg Arg Arg Gln Tyr Arg Glu Tyr Ile Val Arg Asn Glu Val Val
            260                 265                 270

Leu Arg Ala Gly Asp Thr Ile Asn Glu Phe Gly Trp Asp Asn Lys His
        275                 280                 285

Ala Gly Ile Asn Ile Leu Ile Ser Lys Glu Val Leu Met Gly Lys Ala
    290                 295                 300

Asp Tyr Phe Glu Ser Phe Lys Gln Asn Ala Asp Gly Phe Ile Cys Ser
305                 310                 315                 320

Val Leu Pro Gly Leu Ala His Thr Gln Val Gln Tyr Ser Pro Gly Gly
            325                 330                 335

Leu Ile Phe Lys Pro Gly Gly Ser Asn Met Gln His Val Thr Ser Leu
            340                 345                 350

Ser Phe Leu Leu Leu Thr Tyr Ser Asn Tyr Leu Ser His Ala Asn Lys
            355                 360                 365

Asn Val Pro Cys Gly Met Thr Ser Ala Ser Pro Ala Phe Leu Lys Gln
        370                 375                 380

Leu Ala Lys Arg Gln Val Asp Tyr Ile Leu Gly Asp Asn Pro Leu Arg
385                 390                 395                 400

Met Ser Tyr Met Val Gly Tyr Gly Pro Arg Tyr Pro Gln Arg Ile His
                405                 410                 415

His Arg Gly Ser Ser Leu Pro Ser Val Gln Ala His Pro Ala Arg Ile
            420                 425                 430

Gly Cys Lys Ala Gly Ser Arg Tyr Phe Met Ser Pro Asn Pro Asn Pro
            435                 440                 445

Asn Lys Leu Val Gly Ala Val Val Gly Gly Pro Asn Ser Ser Asp Ala
        450                 455                 460

Phe Pro Asp Ser Arg Pro Tyr Phe Gln Glu Ser Glu Pro Thr Thr Tyr
465                 470                 475                 480

Ile Asn Ala Pro Leu Val Gly Leu Leu Ser Tyr Phe Ala Ala His Tyr
                485                 490                 495

<210> SEQ ID NO: 3
<211> LENGTH: 8
<212> TYPE: PRT
<213> ORGANISM: Artificial Sequence
<220> FEATURE:
<223> OTHER INFORMATION: Description of Artificial Sequence: domain
      corresponding to degenerate nucleotides

<400> SEQUENCE: 3

Cys Trp Glu Arg Pro Glu Asp Met
1               5
```